United States Patent [19]

Chan

[11] Patent Number: 4,599,351
[45] Date of Patent: Jul. 8, 1986

[54] FUNGICIDAL 3-(N-ACYL-N-ARYLAMINO) LACTONES

[75] Inventor: David C. K. Chan, Petaluma, Calif.

[73] Assignee: Chevron Research Company, San Francisco, Calif.

[21] Appl. No.: 575,971

[22] Filed: Feb. 1, 1984

Related U.S. Application Data

[63] Continuation-in-part of Ser. No. 292,774, Aug. 14, 1981, abandoned, which is a continuation-in-part of Ser. No. 210,919, Nov. 28, 1980, abandoned.

[51] Int. Cl.$^4$ .................. C07D 307/32; A61K 31/365
[52] U.S. Cl. .................... 314/472; 549/321; 549/63; 514/447
[58] Field of Search .............. 424/279, 275; 549/63, 549/321; 514/472

[56] References Cited

U.S. PATENT DOCUMENTS

| 4,107,323 | 8/1978 | Chan | 424/279 |
| 4,141,989 | 2/1979 | Chan | 424/279 |
| 4,143,155 | 3/1979 | Hubele et al. | 424/303 |
| 4,147,792 | 4/1979 | Kunz | 424/269 |
| 4,165,322 | 8/1979 | Reynolds, Jr. | |
| 4,224,453 | 9/1980 | Reynolds, Jr. et al. | 549/63 |
| 4,233,308 | 11/1980 | Kunz | 424/279 |
| 4,241,078 | 12/1980 | Chan | 424/275 |
| 4,269,849 | 5/1981 | Chan | 424/275 |
| 4,287,210 | 9/1981 | Eckhardt et al. | 424/269 |
| 4,310,463 | 1/1982 | Chan | 549/63 |
| 4,407,817 | 10/1983 | Chan | 424/275 |
| 4,440,780 | 4/1984 | Chan | 424/275 |

FOREIGN PATENT DOCUMENTS 867556 5/1927 Belgium .

Primary Examiner—Jane T. Fan
Attorney, Agent, or Firm—J. A. Buchanan, Jr.; L. S. Squires

[57] ABSTRACT 3-(N-butyryl or valeryl-N-arylamino)-gamma-butyrolactones and their thio analogs. These compounds are useful as fungicides.

13 Claims, No Drawings

FUNGICIDAL 3-(N-ACYL-N-ARYLAMINO) LACTONES

CROSS-REFERENCE TO RELATED APPLICATION

This application is a continuation-in-part of co-pending U.S. application Ser. No. 292,774, filed Aug. 14, 1981 and now abandoned, which in turn is a continuation-in-part of U.S. application Ser. No. 210,919, filed Nov. 28, 1980 and now abandoned.

BACKGROUND OF THE INVENTION

U.S. Pat. No. 3,933,860, issued Jan. 26, 1976, U.S. Pat. No. 4,012,519, issued Mar. 15, 1977, U.S. Pat. No. 4,107,323, issued Aug. 15, 1978 and U.S. Pat. No. 4,141,938, issued Feb. 27, 1979, all to David Cheong King Chan, disclose the use of a large class of 3-(N-acyl-N-arylamino)lactones and 3-(N-acyl-N-arylamino) lactams as protectant fungicides.

U.S. Pat. No. 4,034,108, issued July 5, 1977, to H. Moser, and U.S. Pat. No. 4,015,648, issued May 24, 1977 to H. Moser, disclose the use of N-(methoxycarbonylethyl)-N-haloacetyl-anilines as preventive and curative fungicides.

German Patent Publication Nos. 2,643,403 and 2,643,445, published Apr. 7, 1977, disclose the use of N-(alkylthio-carbonylethyl)acetanilides for controlling fungi, particularly those of the class Phycomycetes.

Netherlands Patent Publication No. 152,849, published Apr. 15, 1977, discloses the use of N-(alkoxymethyl)acetanilides as fungicides.

Belgian Pat. No. 867,556, published Nov. 27, 1978, discloses 3-(N-cyclopropylcarbonyl-N-arylamino)-gamma-butyrolactones.

Belgian Pat. No. 863,615, published Aug. 3, 1978, discloses fungicidal 3-(N-acyl-N-arylamino)-gamma-butyrolactones.

In the aforementioned U.S. Pat. No. 3,933,860, I disclose 3-(N-acyl-N-arylamino)lactones and lactams represented by the Formula (I):

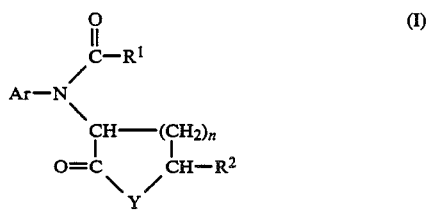

wherein Ar is phenyl or phenyl substituted with 1 to 3 of the same or different substituents selected from fluoro, chloro, bromo, alkyl of 1 to 4 carbon atoms, alkoxy of 1 to 4 carbon atoms or nitro; $R^1$ is alkyl of 1 to 6 carbon atoms, etc.; $R^2$ is hydrogen or alkyl of 1 to 6 carbon atoms; Y is oxygen or N—$R^2$; and n is 1 or 2.

In the aforementioned U.S. Pat. No. 4,107,323, I disclose that compounds of Formula (I), wherein $R^1$ is halomethyl, Y is oxygen and Ar is 2,6-dialkylphenyl, are particularly preferred for their high activity for eradicating and curing established fungal infections, particularly for downy mildew infection of grapevines and late blight infection of tomatoes.

Recently it has been found that subsequent generations of the fungi producing Grape Downy Mildew disease which have been treated with the fungicide most commonly used to control this disease (i.e., N-methoxyacetyl-N-(1-methoxycarbonylethyl)-2,6-dimethylaniline) are appearing to develop resistance to this fungicide. Further, it appears that this acquired resistance also increases the resistance of such fungi to a number of the newer aniline derivative fungicides. If this resistance becomes widespread, it will present considerable problems to the control of this disease.

SUMMARY OF THE INVENTION

It has now been found that among the compounds of the Formula (I) wherein Ar is 2,6-dialkylphenyl, Y is oxygen, n is 0, and $R^1$ is alkyl of 1 to 6 carbon atoms, the compound wherein $R^1$ is propyl or butyl exhibits unexpectedly high fungicidal activity toward Grape Downy Mildew. This is unexpected since the compounds wherein $R^1$ contains less than 3 carbon atoms or more than 4 carbon atoms up to 6 carbon atoms have substantially poorer activity in controlling Grape Downy Mildew and very substantially higher $ED_{50/90}$'s. Further, based on recent fungicide agar studies with N-methoxyacetyl-N-(1-methoxycarbonylethyl)-2,6-dimethylaniline resistant mutant strains of *Pythium ultimum* or *Pythium vexans*, it was found that the fungicidal activity of compounds where $R^1$ is propyl or butyl have substantially better $ED_{50}$'s against resistant fungi than the compounds where $R^1$ has less than 3 carbon atoms. The compounds where $R^1$ has more than four carbon atoms are also less effected by this acquired resistance but their activity against the original fungi is already too low as compared with the $R^1$ propyl and butyl compounds.

DETAILED DESCRIPTION OF THE INVENTION

The 3-(N-butyryl-N-arylamino)lactones and thiolactones of the invention can be represented by the formula:

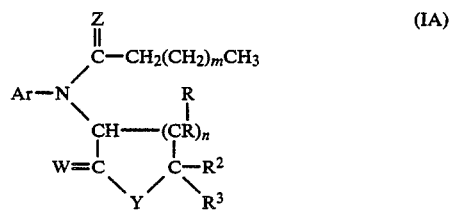

wherein Ar is phenyl or phenyl substituted with 1 to 3 alkyl groups of 1 to 4 carbon atoms; R is the same or different and is hydrogen or alkyl of 1 to 6 carbon atoms; $R^2$ and $R^3$ are individually hydrogen or alkyl of 1 to 6 carbon atoms; m is 1 or 2; n is 1 or 2; and W, Y and Z are oxygen or sulfur.

Representative alkyl groups which R, $R^2$, and $R^3$ may represent are methyl, ethyl, propyl, isopropyl, n-butyl, t-butyl, pentyl, isohexyl, etc.

Representative substituted-phenyl groups which Ar may represent are 2-methylphenyl, 4-methylphenyl, 2,6-diethylphenyl, 2,6-dimethylphenyl, etc. Most preferably Ar is 2,6-dialkylphenyl. Preferably W is oxygen, and R, $R^2$ and $R^3$ are hydrogen.

The preferred compounds of the invention can be represented by the following formula:

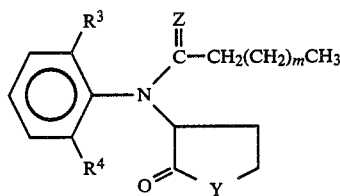

wherein $R^3$ and $R^4$ are independently alkyl having 1 to 4 carbon atoms; and Y and Z are as defined hereinabove.

Preferably Y and Z are oxygen, $R^4$ and $R^5$ are each methyl, and n is 1.

The lactone and thiolactone compounds of the invention may be prepared by methods disclosed in my copending application, Ser. No. 13,856, filed Feb. 22, 1979, the disclosure of which is incorporated by reference, by alkylating an aniline (II) with an alpha-halo-gamma-butyrolactone or alpha-halo-gamma-thiobutyrolactone (III) and subsequently acylating the alpha-(N-arylamino)-gamma-butyrolactone or thiobutyrolactone with an acyl halide (V) to give the 3-(N-acyl-N-arylamino)-gamma-butyrolactone or thiobutyrolactone product (IB), as depicted by the following equations:

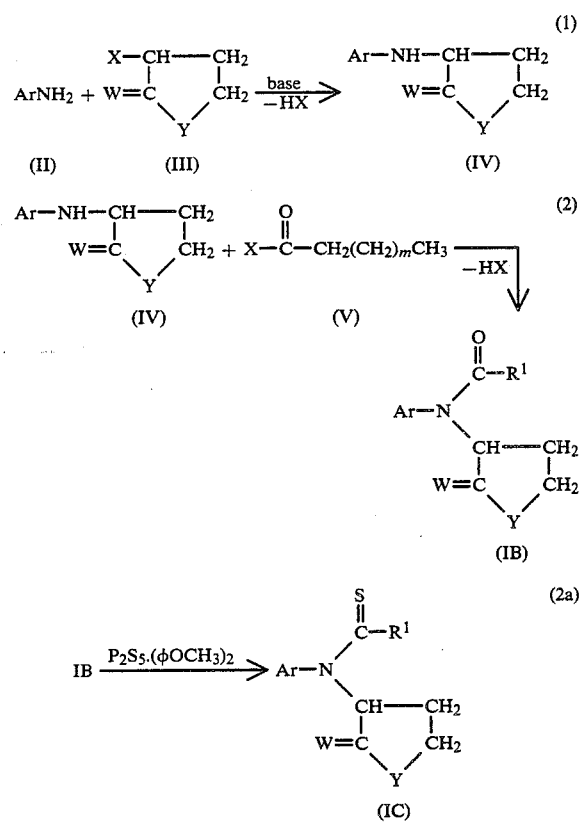

wherein Ar, m, W, Y and Z have the same significance as previously defined; and X is chloro and bromo. The compounds for which n is other than 1 and R, $R^2$ and $R^3$ are other than hydrogen may be made by methods analogous to Reactions (1) and (2).

The alkylation Reaction (1) is conducted in the presence of a base. Suitable bases are inorganic alkali metal carbonates such as sodium carbonates or potassium carbonate or organic amines such as trialkylamines, e.g., triethylamine, or pyridine compounds, e.g., pyridine or 2,6-dimethylpyridine. Generally, substantially equimolar amounts of reactants (II) and (III) and the base are employed. In one modification of the reaction, a molar excess of the aniline reactant (II) is used as the base, and no additional base is employed. The reaction is conducted in inert organic solvent, e.g., apolar diprotic solvents such as dimethylformamide and acetonitrile and aromatic hydrocarbons such as benzene and toluene, at reaction temperatures varying from 25° C. to 150° C., preferably from 50° C. to 150° C. Water may be employed as a co-solvent. The reaction pressure may be atmospheric, subatmospheric or superatmospheric. However, for convenience of conducting the reaction, the pressure is generally atmospheric. The reaction time will, of course, vary depending upon the reactants and the reaction temperature. Generally the reaction time is from 0.25 to 24 hours. The product (IV) is generally purified by conventional procedures, e.g., extraction, distillation or crystallization, before use in the acylation Reaction (2).

Preferred alkylation reaction conditions are given in more detail in the commonly assigned application of Richard N. Reynolds, Jr., entitled "Alkylation of Aniline with a Lactone in the Presence of Water", Ser. No. 847,503, filed Nov. 1, 1977, now U.S. Pat. No. 4,165,322.

The acylation Reaction (2) is conducted by conventional procedures. The reactants (IV) and (V) are generally contacted in substantially equimolar amounts in an inert organic solvent at a temperature of 0° C. to 100° C. Suitable inert organic solvents include ethyl acetate, methylene dichloride, dimethoxyethane, benzene, etc. The product is isolated and purified by conventional procedures such as extraction, distillation, chromatography, crystallization, etc.

When preparing a butyrolactone product [compounds of Formula (IA) wherein Y=O], an organic amine such as a trialkylamine or a pyridine compound may be employed as an acid acceptor. However, when preparing a butyrothiolactone product [compounds of Formula (IA) wherein Y=S], an organic amine should not be employed.

Preferred acylation reaction conditions are given in more detail in the commonly assigned application of Richard N. Reynolds, Jr., Stephen D. Ziman and David C. K. Chan, entitled "Acylation of Lactone-Substituted Aniline Compound in the Absence of an Acid Acceptor", Ser. No. 847,504, filed Nov. 1, 1977, now U.S. Pat. No. 4,224,453, issued Sept. 23, 1980, which procedures are hereby incorporated by reference.

The conversion of the carbonyl compound (IB) to the corresponding thiono compound (IC) according to Reaction (2a) may be accomplished according to conditions described by Shridhar et al., *Organic Preparations and Procedures International*, Volume 12, pp. 203-06 (1980), which is incorporated herein by reference in its entirety.

The compounds of Formula (IA) wherein Y=S are preferably prepared according to the following schematically represented process:

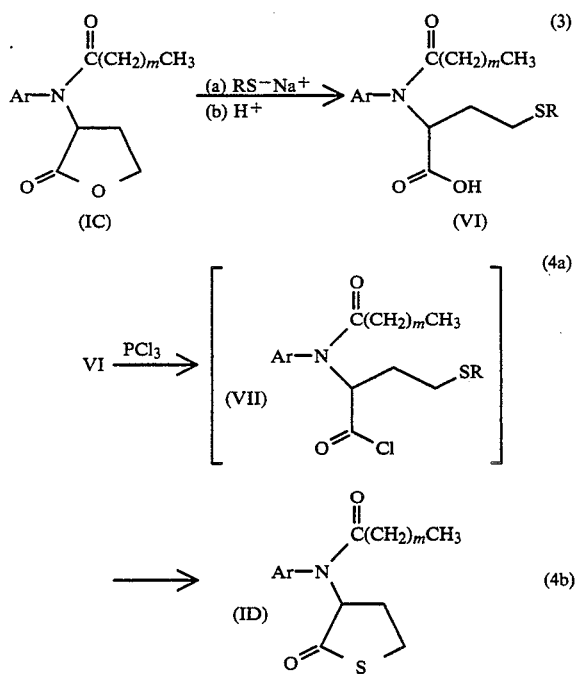

The compound of the Formula (IC) is first treated with the salt, preferably the sodium salt, of an alkyl mercaptan, RSNa, wherein R contains from 1 to 10 carbon atoms. Although the sodium salt of the alkyl mercaptan is preferred, other monovalent cation salts may be used, such as the potassium, lithium or ammonium salt. The acid product of this first reaction is then treated with a reagent, such as phosphorus trichloride, which is capable of converting a carboxylic acid to its corresponding acid halide.

Reaction (3) may be performed in a suitable inert solvent at from about 0° C. to 100° C., preferably in the range 40° C. to 80° C. Substantially equimolar portions of the butyrolactone (IC) and salt of the alkyl mercaptan (RSNa) are used. Suitable solvents include dimethoxyethane, chlorinated hydrocarbons, dioxane, and tetrahydrofuran. The reaction pressure is not critical and may be conveniently selected. Generally, atmospheric pressure is used. The reaction is generally complete within one hour. The product acid (VI) may be isolated by conventional procedures such as extraction, filtration, chromatography, etc. The nature of the salt of the alkyl mercaptan, RSNa, is not particularly critical. Tertiary alkyl mercaptans are preferable to secondary and primary alkyl mercaptans.

Reaction (4a) is shown above as performed with phosphorus trichloride, however, any reagent known to convert carboxylic acid to acid halides may be used. Examples of such reagents are thionyl chloride, phosphorus pentachloride and oxalyl chloride. Reaction (4a) may also be conducted with the corresponding acid salt of the free acid (VI).

Reaction (4a) may be conducted in an inert solvent from about 0° C. to 20° C. When conducted at ambient temperature, upon addition of PCl₃, the reaction mixture will warm to about 40° C. An excess of the stoichiometric amount of PCl₃ is used.

After addition of PCl₃, the mixture is stirred to effect the cleavage Reaction (4b). This reaction may be conducted from about −6° C. to about 80° C., preferably at 8° C. to 14° C. The thiolactone product (ID) is separated from the reaction mixture by conventional methods, i.e., extraction, filtration, chromatography, crystallization, etc.

Particularly preferred solvents for the process (4a) and (4b) are dialkyl glycols, preferably dimethoxyethane, and chlorinated hydrocarbons, preferably methylene chloride. Reactions (4a) and (4b) may be carried out at any convenient pressure, preferably atmospheric pressure.

While use of a solvent is preferred in the practice of Reactions (4a) and (4b), in another embodiment, the PCl₃ may be added directly to the acid (VI), especially if the acid is a liquid. The thiolactone product (ID) may then be isolated by conventional purification procedures.

The preferred molar ratio for Reaction (3) is 1:1 for the starting lactone (IC) and mercaptide salt. For Reaction (4a), if phosphorus trichloride is used, the stoichiometric molar ratio of 3:1 for acid (VI) to PCl₃ may be used. An acid (VI) to PCl₃ molar ratio of 3:2 is preferred.

Further information concerning the aforementioned process can also be had by reference to commonly assigned U.S. application Ser. No. 374,673, filed May 4, 1982 by F. J. Freenor III, which description is hereby incorporated by reference.

Utility

The compounds of the invention are useful for controlling fungi, particularly plant fungal infections. For example, the activity of the preferred compounds of the invention is highly specific for certain fungal diseases such as downy mildews, e.g., *Plasmopara viticola* (grapes) and *Peronospora parasitica* (cabbage and collard).

The compounds of the invention are particularly useful fungicides because they cure established fungal infections. This permits economical use of the fungicides of the invention, because they need not be applied to plants unless fungal infection actually occurs. Thus, a preventative program of applying fungicides against potential fungal infection is not necessary.

When used as fungicides, the compounds of the invention are applied in fungicidally effective amounts to fungi and/or their habitats, such as vegetative hosts and nonvegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, wettable, inorganic diluents. Typical wetting, dispersing or emulsifying agents include, for example: the aryl and alkylaryl sulfonates and their sodium salts, alkylamide sulfonates, including fatty methyl taurides: alkylaryl polyether alcohols, sulfated higher alcohols and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% in 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLES

The preparation and utility of the compounds of the invention are illustrated by the following examples.

EXAMPLE 1

Preparation of 3-(N-butyryl-N-2,6-dimethylphenylamino)-gamma-butyrolactone

A slurry of 12.2 g (0.1 mol) 2,6dimethylaniline, 16.5 g (0.1 mol) alpha-bromo-gamma-butyrolactone, 10.6 g (0.1 mol) sodium carbonate and 150 ml dimethylformamide is heated at 125° C.–140° C. for 21 hours. The reaction mixture is then diluted with water and extracted with benzene. The benzene extracts are washed with water, dried over magnesium sulfate and evaporated to give an oil. The oil is chromatographed on a silica gel column. 3-(N-2,6-dimethylphenylamino)-gamma-butyrolactone, m.p. 85° C.–87° C., is eluted from the column with 50:50 hexane/ether.

A solution of 6.2 g (0.03 mol) 3-(N-2,6-dimethylphenylamino)-gamma-butyrolactone, 3.5 g (0.033 mol) butyryl chloride, 2.6 g (0.033 mol) pyridine and 150 ml ethyl acetate is stirred overnight at 25° C. and then at 50° C.–75° C. for 3 hours. After cooling, the reaction mixture is washed with water, diluted with methylene chloride, washed with water, 10% aqueous sodium bicarbonate, washed with water, dried over magnesium sulfate and evaporated to give a solid residue. The residue is crystallized from ethyl ether to give the title compound. By replacing butyryl chloride with valeryl chloride the corresponding valeryl homolog of the product is prepared.

EXAMPLE 2

Preparation of 2-(N-butyryl-2,6-dimethylanilino)-4-(tert-butylthio)-butanoic acid To 952 g (17.02 mol) sodium methoxide in 3.8 l dimethoxyethane is added in portions 1590 g (17.62 mol) t-butylmercaptan and 3.8 l dimethoxyethane. The mixture is stirred until it cooled to about 40° C.

3-(N-butyryl-2,6-dimethylphenylanilino)-butyrolactone (4443 g, 16.0 mol), Example 1, is added in portions to the reaction mixture and heated externally to 60° C.–80° C. The mixture is stirred and allowed to cool to 60° C., then is poured into 2.8 l iced water.

The mixture is extracted with toluene, and the extracts are back-washed with water. Each water backwash is added back to the aqueous phase. The aqueous phase is acidified (pH 1) with 19% HCl, then extracted twice with methylene chloride. The organic phases ($CH_2Cl_2$) are combined, washed with water, dried ($MgSO_4$), filtered and stripped to yield the title product as an oil.

EXAMPLE 3

Preparation of 3-(N-butyryl-2,6-dimethylanilino)-butyrothiolactone

The acid produced in Example 2 is dissolved in 2 l methylene chloride in a flask equipped with a condenser and cooled to 5° C. in a dry ice/acetone bath. Then $PCl_3$ (256 g) is added dropwise. The temperature is maintained below 10° C. during addition. The mixture is stirred overnight at room temperature.

The mixture is poured into 7.7 l ice water and 2 l methylene chloride and the organic layer is collected. After two more extractions with methylene chloride, the organic phases are combined, washed with a 50% mixture of saturated NaCl solution and water, dried (MgSO4, silica gel), filtered and stripped. The resultant oil is slurried in isopropyl alcohol, filtered, and the solid rinsed with isopropyl alcohol then with hexane to yield the title product.

EXAMPLE 4

Eradicant Grape Downy Mildew Control

Compounds of the invention were tested for the eradicant control of the Grape Downy Mildew organism *Plasmopara viticola*. Detached leaves of between 70 and 80 mm diameter of 7-week-old *Vitis vinifera* cultivar Emperor grape seedlings were used as hosts. The leaves were inoculated with the organism and placed in an environment chamber and incubated at 18° C.–22° C. and at about 100% relative humidity for 1 to 2 days. The leaves were then sprayed with a solution of the test compound in acetone, water and a small amount of a nonionic emulsifier. The sprayed leaves were then maintained at 18° C.–22° C. and at about 100% relative humidity. Seven to nine days after inoculation, the amount of disease control was determined. The percent disease control provided by the compound of Example 1 was based on the percent disease reduction relative to nontreated check plants. The title compound of Example 1 exhibited 100% control at 250, 100 and 40 ppm. The compound 3-(N-valeryl-N-2,6-dimethylphenylamino)-gamma-butyrolactone exhibited 100% control at 100 ppm and 92% control at 40 ppm.

EXAMPLE 5

Preventative Control Grape Downy Mildew and Tomato Late Blight Disease

The compounds indicated in the following tables were tested for preventative control of the Grape Downy Mildew organism *Plasmopara viticola*, using either *Vitis vinifera* cultivar Emperor grape seedlings or detached leaves therefrom, between 70 and 85 mm in diameter, as hosts. The seedlings or leaves were sprayed with a solution of the test compound in acetone at various concentrations. The sprayed seedlings or leaves were dried, inoculated with a spore suspension of the organism, placed in a humid environmental chamber and incubated at 18° C.–22° C. and about 100% relative humidity. Seven to nine days after inoculation, the amount of disease control was determined. The percent disease control provided by the compound of Example 1 was based on the percent disease reduction relative to untreated check plants.

The tests for Tomato Late Blight control were performed according to the following procedure.

Five- to six-week-old tomato (cultivar Bonny Best) seedlings were used. The tomato plants were sprayed with a 250-ppm suspension of the test compound in acetone, water and a small amount of a non-ionic emulsifier. The sprayed plants were then inoculated one day later with the organism, placed in an environmental chamber and incubated at 66° F.–68° F. and 100% relative humidity for at least 16 hours. Following the incubation, the plants were maintained in a greenhouse at 60–80% relative humidity for approximately 7 days. The percent disease control provided by a given test compound was based on the percent disease reduction relative to untreated check plants.

The tests reported in Table I were conducted at different times but following the same procedures described hereinabove. Application of the test compounds reported in Table I were at 250 ppm unless otherwise indicated in parentheses.

TABLE I

Fungicidal Efficacy - @ 250 ppm

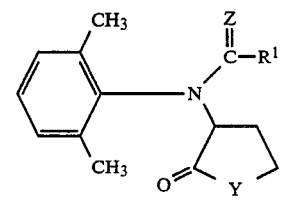

| R¹ | Y | Z | GDM | TLB |
|---|---|---|---|---|
| CH3 | O | O | 42 (100 ppm) | 79 (100 ppm) |
| C2H5 | O | O | — | 23 |
| CH2CH2CH3 | O | O | 100 | 99 |
| CH(CH3)2 | O | O | 0 | 23 |
| CH2CH(CH3)2 | O | O | 96 | 0 |
| C(CH3)3 | O | O | — | 0 |
| CH2CH2CH3 | S | O | 99 | 35 |
| CH2CH2CH3 | O | S | 100 | 96 |
| (CH2)3CH3 | O | O | 100 | 96 |
| (CH2)4CH3 | O | O | 100 | 91 |

GDM = Grape Downy Mildew (*Plasmopara viticola*)
TLB = Tomato Late Blight (*Phytophthora infestans*)

EXAMPLE 6

In this example, follow-up tests for Grape Downy Mildew preventative activity and Tomato Late Blight preventative activity were conducted on the compounds of the present invention wherein Y is —O— and R² is H and n is 1 and the corresponding R¹ is ethyl, propyl, n-butyl and n-pentyl. The same procedures as described above with respect to these tests were followed with the exception of the specific dosages used. These tests were generally conducted at different times with the exception that where the results for two compounds are reported under the same test number, it indicates that the testing was conducted side by side as part of the same test grouping. It is also noted that in order for the test results to be representative, the degree of infection in the nontreated check plants should be in the range of 30% to 80% infection. Both higher and lower degrees of infection give nonrepresentative results. The results of these tests are set forth in Table II hereinbelow.

As can be seen from Table II, the compounds of the present invention generally exhibited substantially superior Grape Downy Mildew preventive activity in these tests and, where plotted, superior (lower) ED$_{50/90's}$. The Tomato Late Blight activity was also generally superior for the present compounds but not as outstanding as the Grape Downy Mildew activity.

TABLE II

PREVENTATIVE FUNGICIDAL ACTIVITY

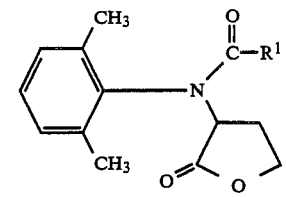

Preventative Fungicidal Activity Against
Grape Downy Mildew Disease ("GDM")

Test 1

TABLE II-continued
PREVENTATIVE FUNGICIDAL ACTIVITY

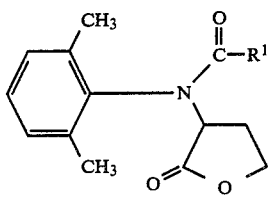

| Dosage | Percent Control of GDM | |
|---|---|---|
| ppm | $R^1$ is $-C_2H_5$ | $R^1$ is $-CH_2CH_2CH_3$ |
| 250 | 100 | 100 |
| 100 | 96 | 100 |
| 40 | 98 | 99 |
| 16 | — | — |
| 6.4 | — | — |
| $ED_{50/90}$ | N.C.* | N.C.* |

Degree of infection in check plants: 63%.

Test 2

| Dosage | Percent Control of GDM | |
|---|---|---|
| ppm | $R^1$ is $-C_2H_5$ | $R^1$ is $-CH_2CH_2CH$ |
| 250 | — | — |
| 100 | — | — |
| 40 | 80 | 96 |
| 16 | 44 | 82 |
| 6.4 | 20 | 43 |
| $ED_{50/90}$ | 17.5/72 | 7.3/14 |

Degree of infection in check plants: 79%.

Test 3

| Dosage | Percent Control of GDM | |
|---|---|---|
| ppm | $R^1$ is $-(CH_2)_3CH_3$ | $R^1$ is $-(CH_2)_4CH_3$ |
| 250 | — | — |
| 100 | — | — |
| 40 | — | — |
| 16 | 100 | 37 |
| 6.4 | 60 | 27 |
| 2.5 | 54 | 16 |
| $ED_{50/90}$ | 3.7/6.8 | 38/>100 |

Degree of infection in check plants: 63%.

Preventative Fungicidal Activity Against Tomato Late Blight Disease ("TLB")

Test 4

| Dosage | Percent Control of TLB | |
|---|---|---|
| ppm | $R^1$ is $-C_2H_5$ | $R^1$ is $-CH_2CH_2CH_3$ |
| 250 | 80 | 94 |
| 100 | 54 | 76 |
| 40 | 0 | 48 |
| 16 | 0 | 0 |
| $ED_{50/90}$ | 105/380 | 46/190 |

Degree of infection in check plants: 63%.

Test 5 - TLB

| Dosage | Percent Control of TLB | |
|---|---|---|
| ppm | $R^1$ is $-(CH_2)_3CH_3$ | $R^1$ is $-(CH_2)_4CH_3$ |
| 250 | — | — |
| 100 | — | — |
| 40 | 42 | 37 |
| 16 | 28 | 3 |
| 6.4 | 8 | 7 |
| $ED_{50}$ | 45 | 55 |

Degree of infection in check plants: 60%.

*N.C.: Not calculated.

EXAMPLE 7

This example compares the fungitoxicity of various aniline derivatives, including the present compounds, with N-methoxyacetyl-N-(1-methoxycarbonylethyl)-2,6-dimethylaniline, hereinafter referred to in this example as the "Control", against resistant mutants of Pythium ultimum and/or Pythium vexans and also against the sensitive naturally occurring species of these fungi. The control resistant mutants were obtained from the laboratory of L. V. Edgington of the University of Guelph.

This evaluation was conducted by preparing ethanol solutions of the respective compounds to be tested, including the "Control". One ml of the ethanol solutions was blended with 100 ml of melted V-8 juice agar. The medium was poured in plates and cooled. Plugs of agar plated mycelial cultures of the respective fungi were taken at the periphery with a #2 cork borer and placed upside down in the center of the treated agar plates. Measurements of surface growth (diameter in mm) were taken in two directions. These were averaged and the 8 mm diameter of inoculating plug was subtracted. The data was converted to dosage response curves on log probability graph paper and in turn to $ED_{50}$ values. Each treatment contained three replicates and was tested one or more times. Dosage response curves included four dosages of a compound.

The results of this evaluation are given in Table III hereinbelow. The ratio of $ED_{50}$-resistant to $Ed_{50}$-sensitive is an indication of the degree that the compounds fungitoxicity will be affected by Control resistance developed by the fungi. The smaller the ratio, the more likely the compound is to overcome the Control resistance block. (The variation in the ratio between the two mutant species suggests that the developed resistance varies between the two mutants.)

As can be seen from this table, although the relative $ED_{50}$ ratios for the $R^1$ is ethyl compound is very good, the actual $ED_{50}$ values are more than twice the $ED_{50}$ for the $R^1$ is propyl compound in the case of P. ultimum (resistant) and more than ten times in the case of P. ultimum (sensitive). The $ED_{50}$ of the $R^1$ is ethyl compound is more than three times that of the $R^1$ is propyl compound with respect to P. vexans (resistant) and more than two times in the case of P. vexans (sensitive). In the case of the $R^1$ is butyl compound, the $ED_{50}$ of the R is ethyl compound is more than three times that of the $R^1$ is butyl compound with respect to P. vexans (resistant) and more than ten times with respect to P. vexans (sensitive). The compound wherein $R^1$ is pentyl has an excellent $ED_{50}$ R/S P. vexans ratio and $ED_{50}$ P. vexans (resistant). However, even though the fungitoxicity of this compound appears to be substantially less affected by the acquired Control resistance than any of the compounds in Table III, the actual base $ED_{50}$ relative to Grape Downy Mildew producing fungi (natural) shown in Table II of Example 6, hereinabove, is already four to ten times higher than the $R^1$ is propyl or butyl compounds of the invention.

The compounds of the present invention exhibit very good effectiveness in controlling Grape Downy Mildew caused by non-mutant fungi (see Table II, Example 6) and further as can be seen from Table III are less affected by mutant Control resistance than is the Control of two of the leading new Grape Downy Mildew aniline derivative fungicides represented by the $R^1$ is $-CH_2OCH_3$ and $R^1$ is $-CH_2Cl$ compounds.

TABLE III

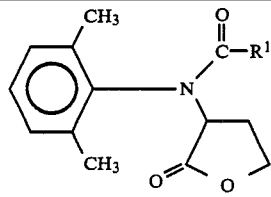

| R¹ | *Pythium ultimum* | | | *Pythium vexans* | | |
|---|---|---|---|---|---|---|
| | Sensitive (Naturally Occurring) ED$_{50}$ ppm | Resistant ED$_{50}$ ppm | ED$_{50}$ Ratio R/S | Sensitive (Naturally Occurring) ED$_{50}$ ppm | Resistant ED$_{50}$ ppm | ED$_{50}$ Ratio R/S |
| CONTROL | 0.036 | 940 | 26,000 | 0.075 | 635 | 8,467 |
| —CH$_2$OCH$_3$ | 0.005 | 800 | 160,000 | 0.15 | 400 | 8,000 |
| —CH$_2$Cl | 0.005 | 120 | 24,000 | 0.19 | 145 | 763 |
| —CH$_2$CH$_3$ | 0.26 | 210 | 808 | >1.0 | 140 | <140 |
| —(CH$_2$)$_2$CH$_3$ | 0.02 | 95 | 4,750 | 0.43 | 43 | 100 |
| —(CH$_2$)$_3$CH$_3$ | N.T. | N.T. | — | 0.10 | 40 | 400 |
| —(CH$_2$)$_4$CH$_3$ | N.T. | N.T. | — | 0.56 | 16 | 29 |

Obviously, many modifications and variations of the invention, described hereinabove and below in the claims, can be made without departing from the essence and scope thereof.

What is claimed is:

1. A method for the control of Grape Downy Mildew comprising contacting said mildew or its habitat with a fungicidally effective amount of a compound of the formula:

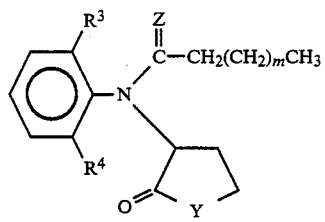

wherein R³ and R⁴ are independently alkyl having 1 to 4 carbon atoms; Y is oxygen; m is 1 or 2; and Z is oxygen or sulfur.

2. A method according to claim 1 wherein Z is oxygen.
3. A method according to claim 2 wherein Ar is 2,6-dimethylphenyl.
4. A method according to claim 3 wherein m is 1.
5. A method according to claim 3 wherein m is 2.
6. A compound of the formula:

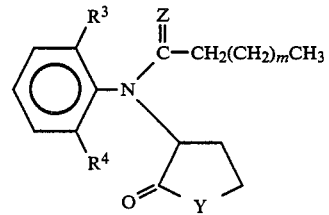

wherein R³ and R⁴ are independently alkyl having 1 to 4 carbon atoms; Y is oxygen; m is 1 or 2; and Z is oxygen or sulfur.

7. The compound of claim 6 wherein Z is oxygen.
8. The compound of claim 6 wherein R³ and R⁴ are each methyl.
9. The compound of claim 8 wherein m is 1.
10. The compound of claim 8 wherein m is 2.
11. The compound of claim 6 wherein, Z is sulfur, and R³ and R⁴ are each methyl.
12. The compound of claim 11 wherein m is 1.
13. The compound of claim 11 wherein m is 2.

* * * * *